US007129086B2

(12) United States Patent
Torok-Storb et al.

(10) Patent No.: US 7,129,086 B2
(45) Date of Patent: *Oct. 31, 2006

(54) HUMAN MARROW STROMAL CELL LINES WHICH SUSTAIN HEMATOPOIESIS

(75) Inventors: Beverly Torok-Storb, Seattle, WA (US); Bryan A. Roecklein, Seattle, WA (US); Gretchen Johnson, Issaquah, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/162,825

(22) Filed: Jun. 4, 2002

(65) Prior Publication Data

US 2002/0197717 A1 Dec. 26, 2002

Related U.S. Application Data

(60) Continuation of application No. 09/583,215, filed on May 30, 2000, now abandoned, which is a continuation of application No. 08/455,577, filed on May 31, 1995, now Pat. No. 6,103,522, which is a division of application No. 08/277,883, filed on Jul. 20, 1994, now abandoned.

(51) Int. Cl.
*C12N 5/00* (2006.01)
(52) U.S. Cl. .................. 435/366; 435/325; 435/404; 435/70.1; 435/372; 435/405
(58) Field of Classification Search ............. 435/325, 435/404, 70.1, 366, 372, 405
See application file for complete search history.

(56) References Cited

U.S. PATENT DOCUMENTS

| 5,004,681 | A |   | 4/1991 | Boyse et al. |         |
|-----------|---|---|--------|--------------|---------|
| 5,215,927 | A |   | 6/1993 | Berenson et al. |     |
| 5,322,787 | A |   | 6/1994 | Martin et al. |       |
| 5,879,940 | A | * | 3/1999 | Torok-Storb et al. | 435/404 |
| 6,103,522 | A | * | 8/2000 | Torok-Storb et al. | 435/325 |

OTHER PUBLICATIONS

Berenson et al., "Transplantation of Stem Cells Enriched by Immunoadsorption," *Adv. Bone Marrow Purging & Processings*, N.Y.: Wiley-Liss, p. 449 (1992).
Charbord et al., "The Cytoskeleton of Stromal Cells from Human Bone Marrow Cultures Resembles that of Cultured Smooth Muscle Cells," *Exp. Hematol. 18*:276 (1990).
Chiang et al., "Development of an Immortalized Human Bone Marrow Stromal Cell Line (cv25ah-3) That Supports Both Human Myelopoiesis and Lymphopoiesis," *Blood 84* (10 Supp 1):48A (1994).

Cicutinni et al., "Support of Human Cord Blood Progenitor Cells on Human Stromal Cell Lines Transformed by $SV_{40}$ Large T Antigen under the Influence of an Inducible (Metallothionein) Promoter," *Blood 80*:102 (1992).
Clark et al., "Cell Adhesion in the Stromal Regulation of Haemopoiesis," *Bailliere's Clin. Haematol. 5*:619 (1992).
Deryugina et al., "Stromal Cells in Long-Term Cultures: Keys to the Elucidation of Hematopoietic Development?" *Critical Rev. Immunol. 13*:115 (1993).
Dorshkind, "Regulation of Hemopoiesis by Bone Marrow Stromal Cells and their Products," *Ann. Rev. Immunol. 8*:111 (1990).
Eaves et al., "Mechanisms that Regulate the Cell Cycle Status of Very Primitive Hematopoietic Cells in Long-Term Human Marrow Cultures. II. Analysis of Positive and Negative Regulators Produced by Stromal Cells within the Adherent Layer," *Blood 78*:110 (1991).
Eaves et al., "Methodology of Long-Term Culture of Human Hemopoietic Cells," *J. Cult. Metho. 13*:55 (1991).
Fibbe et al., "Proliferation of Hematopoietic Progenitor Cells in Long Term Bone Marrow Cultures (LTBMC) and the Release of Colony-Stimulating Factors (CSFs) By Human Stromal Cells is Stimulated by Interleukin-1 Beta (IL-1)," *Lymphokine Res. 7(3)*:290 (1988).
Galmiche et al., "Stromal Cells from Human Long-Term Marrow Cultures are Mesenchymal Cells that Differentiate Following a Vascular Smooth Muscle Differentiation Pathway," *Blood 82*:66 (1993).
Galy et al., "Untransfected and SV40-transfected fetal and postnatal human thymic stromal cells," *Thymus 22*:13-33 (1993).
Halbert et al., "The E7 Gene of Human Papillomavirus Type 16 is Sufficient for Immortalization of Human Epithelial Cells," *J. Virol. 65*:473 (1991).
Harigaya et al., "Generation of Functional Clonal Cell Lines from Human Bone Marrow Stromal," *Proc. Natl. Acad. Sci. USA 82*:3477 (1985).
Heinrich et al., "Constitutive Expression of Steel Factor Gene by Human Stromal Cells," *Blood 82*:771 (1993).

(Continued)

*Primary Examiner*—Leon B. Lankford, Jr.
(74) *Attorney, Agent, or Firm*—Townsend and Townsend and Crew LLP

(57) ABSTRACT

Immortalized human stromal cell lines sustain and expand human hematopoietic precursor cells. The precursor cells are obtained from a blood product and inoculated into a culture medium conditioned by exposure to a human stromal cell line. Preferred human stromal cell lines secrete SCF, LIF, MIP1α, and IL-6, as exemplified by a human stromal cell line designated HS-1. The conditioned culture medium may be supplemented with additional growth factors, such as interleukin-3. After expansion the human hematopoietic precursor cells are harvested and returned to a patient or frozen and stored. The immortalized human stromal cell lines can also be used as feeder layers in ex vivo bone marrow cultures or in colony forming assays.

5 Claims, 4 Drawing Sheets

OTHER PUBLICATIONS

Kittler et al., "Biologic Significance of Constitutive and Subliminal Growth Factor Production by Bone Marrow Stroma," *Blood* 79:3168 (1992).

Lanotte et al., "Histochemical and Ultrastructural Characteristics of a Cell Line from Human Bone Marrow Stroma," *J. Cell Sci. 50*:281 (1981).

Novotny et al., "Cloned Stromal Cell Lines Derived from Human Whitlock/Witte-type Long-term Bone Marrow Cultures," *Exp. Hematol. 18*:775 (1990).

Nuttall et al., "Gene Expression in 'Immortalized' Human Marrow Stromal Stem Cell-Lines," *J. Bone & Mineral Res. 7(S1)*:PS201 (1992).

Ogawa, "Differentiation and Proliferation of Hematopoietic Stem Cells," *Blood 81*:2844 (1993).

Quesenberry, "Stroma-Dependent Hematolymphopoietic Stem Cells," *Curr. Topics Microbiol. Immunol. 177*:151 (1992).

Rinehart et al., "In SV40-immortalized human endometrial stromal cells, anchorage independence correlates with endogenous IL-1 expression and is induced by IL-1," *Proc. of the Amer. Assoc. for Cancer Res. 34*:148 (1993).

Roecklein and Torok-Storb, "Functionally Distinct Human Marrow Stromal Cell Lines Immortalized by Transduction With the Human Papilloma Virus E6/E7 Genes," *Blood 85(4)*:997-1005 (1995).

Ryan et al., "HK-2: An Immortalized Proximal Tubule Epithelial Cell Line from Normal Adult Human Kidney," *Kidney Int. 45*:48 (1994).

Singer et al., "Simian Virus 40-Transformed Adherent Cells from Human Long-term Marrow Cultures: Cloned Cell Lines Produce Cells with Stromal and Hematopoietic Characteristics," *Blood 70(2)*:464-474 (1987).

Simmons et al., "Identification of Stromal Cell Precursors in Human Bone Marrow by a Novel Monoclonal Antibody, STRO-1," *Blood 78*:55-62 (1991).

Slack et al., "Regulation of Cytokine and Growth Factor Gene Expression in Human Bone Marrow Stromal Cells Transformed with Simian Virus 40," *Blood 75(12)*:2319 (1990).

Song et al., "Radioresistant Murine Marrow Stromal Cells: A Morphologic and Functional Characterization," *Exp. Hematol. 12*:523 (1984).

Sutherland et al., "Functional Characterization of Individual Human Hematopoietic Stem Cell Cultured at Limiting Dilution on Supportive Marrow Stromal Layers," *Pros. Natl. Acad. Sci. USA 87*:3584 (1990).

Thalmeir et al., "Establishment of Two Permanent Human Bone Marrow Stromal Cell Lines with Long-Term Post Irradiation Feeder Capacity," *Blood 83*:1799 (1994).

Tsai et al., "Isolation of a Human Stromal Cell Strain Secreting Hemopoietic Growth Factors," *J. Cell Physiol. 127*:137 (1986).

Verfaille, "Soluble Factor(s) Produced by Human Bone Marrow Stroma Increase Cytokine-Induced Proliferation and Maturation of Primitive Hematopoietic Progenitors While Preventing Their Terminal Differentiation," *Blood 82(7)*:2045-2053 (1993).

Weber et al., "Use of Episomal Vectors for Gene Expression in Human Bone Marrow Stromal Cells," *J. Cell. Biochem. 13C*:48 (Abstract H 346) (1989).

Zipori et al., "Cultured Mouse Marrow Cell Lines: Interactions Between Fibroblastoid Cells and Monocytes," *J. Cell Physiol. 118*:143 (1984).

Ziport et al., "Cultured Mouse Marrow Stromal Cell Lines, II. Distinct Subtypes Differing in Morphology Collage Types, Myelopoietic Factors, and leukemic Cell Growth Modulating Activities," *J. Cell Physiol. 122*:81 (1985).

\* cited by examiner

HUMAN MARROW STROMAL CELL LINES WHICH SUSTAIN HEMATOPOIESIS This application is a continuation of and claims the benefit of U.S. patent application Ser. No. 09/583,215, filed May 30, 2000, now abandoned which is a continuation of U.S. patent application Ser. No. 08/455,577, filed May 31, 1995 and issued as U.S. Pat. No. 6,103,522, which is a divisional application of U.S. patent application Ser. No. 08/277,883, filed Jul. 20, 1994, all incorporated herein by reference.

GOVERNMENT SUPPORT

The present invention was made with support under grant no. DK34431 received from the U.S. National Institutes of Health. The U.S. Government has certain rights in this invention.

BACKGROUND OF THE INVENTION

Hematopoietic cells are believed to arise in the bone marrow from a totipotent stem cell. The stem cell is able to renew itself as well as to give rise to progenitor cells such as the erythroid progenitors and myeloid progenitors. The progenitor cells, in turn, give rise to differentiated cells which are morphologically recognizable as belonging to a certain lineage such as the erythroid, megakaryocytic, myeloid, and lymphoid lineages, and which have a limited or no capacity to proliferate. In humans, stem cells and progenitor cells express the CD34 antigen, while more differentiated hematopoietic cells do not.

Stem cells and progenitor cells do not execute their development programs autonomously. Activities produced in the marrow microenvironment signal the progenitor cells to divide and differentiate. Thus, defining the functional components of the bone marrow microenvironment is a prerequisite to understanding how the proliferation and differentiation of progenitor cells is coordinately regulated. The cellular complexity of the marrow microenvironment has been demonstrated both in situ and in vitro by a variety of histochemical techniques (Lichtman, *Exp. Hematol.* 9:391 (1981), and Allen et al., *Exp. Hematol.* 12: 517 (1984)). The marrow microenvironment is comprised of both hematopoietic and stromal or mesenchymal derived cells. The stromal cells include endothelial cells that form the sinuses and adventitial reticular cells that have characteristics consistent with adipocytes, fibroblasts, and muscle cells (Charbord et al., *Blood* 66: 1138 (1985), and Charbord et al., *Exp. Hematol,* 18: 276 (1990)). Numerous advances in recent years have provided considerable information on the ontogeny and development of hematopoietic cells; however, ontogeny of the stromal components and their precise role in controlling hematopoiesis has proven elusive (Ogawa, *Blood* 81: 2844 (1993); Muller-Sieburg et al., *Critical Rev. Immunol.* 13: 115 (1993); and Dorshkind, *Ann, Rev. Immunol.* 8: 111 (1990)).

Long term cultures of marrow cells are an in vitro approximation of the in vivo marrow microenvironment and have been informative with respect to the identification of growth factors, adhesion proteins and extracellular matrix proteins that mediate the interaction between the hematopoietic cells and the stromal elements (Muller-Sieburg et al., supra; Dorshkind, supra; Liesveld et al., *Exp. Hematol.* 9: 391 (1981); Kittler et al., *Blood* 79: 3168 (1992); Eaves et al., *Blood* 78: 110 (1991); Clark et al., *Bailliere's Clin. Haematol.* 5: 619 (1992); and Heinrich et al., *Blood* 82: 771 (1993)). One improvement to this system was the use of stromal precursors, positive for the STRO-1 antigen, to initiate long term cultures (LTC); STRO-1 positive stromal precursors are devoid of myeloid components and less heterogeneous than primary cultures, but are still capable of supporting hematopoiesis (Simmons and Torok-Storb, *Blood* 78: 55–62 (1991)). However, both the STRO-1 initiated cultures and the primary LTC are too complex to delineate contributions from individual cell types. Moreover, primary cultures can be highly variable and change with time, further complicating the identification of stromal cells that have a role in controlling hematopoiesis.

Immortalized stromal cell lines have been used to circumvent some of these problems. Numerous spontaneous murine cell lines have been established (Zipori et al., *J. Cell Physiol,* 118: 143 (1984); Zipori et al., *J. Cell Physiol.* 122: 81 (1985); and Song et al., *Exp. Hematol.* 12:523 (1984)), however, unlike mouse lines human cell lines undergo senescence unless first immortalized by transformation with a retrovirus (Lanotte et al., *J. Cell Sci.* 50: 281 (1981)). The few human bone marrow stromal cell lines that are available were established using the SV40 virus large T antigen (Harigaya et al., *Proc. Natl. Acad. Sci. USA* 82: 3477 (1985); Tsai et al., *J. Cell Physiol.* 127: 137 (1986); Novotny et al., *Exp. Hematol.* 18: 775 (1990); Slack et al., *Blood* 75: 2319 (1990); Singer et al., *Blood* 70: 464 (1987); Cicutinni et al., *Blood* 80: 102 (1992); and Thalmeir et al., *Blood* 83: 1799 (1994)). Some of these lines are promising with respect to the maintenance of hematopoietic cells; unfortunately, some also display transformed phenotypes which limits their usefulness for extrapolation to the normal marrow microenvironment (Novotony, Supra).

The ability to culture hematopoietic cells and their precursors, derived from the bone marrow, peripheral blood, or umbilical cord blood of a patient or donor, offers the potential to overcome the disadvantages of immunosuppressive or immunodestructive therapies which are often used in the treatment of cancer and other life-threatening diseases. Cultured hematopoietic cells can be used as an important source of proliferating cells to reconstitute a patient's blood-clotting and infection-fighting functions subsequent to therapy. In addition, the ability to expand hematopoietic cells and their precursors in vitro may relieve dependence on bone marrow aspiration or multiple aphereses as the only means of obtaining sufficient cells for transplantation.

Early work in the field of hematopoietic stem cell culture centered around the culture of murine bone marrow aspirates in agar gel or liquid medium. Unfractionated bone marrow (including stem cells, progenitor cells, more differentiated hematopoietic cells, and stromal elements) was used to inoculate the cultures, but they were generally short-lived and resulted in little or no increase in cell number, particularly in the stem cell and progenitor compartments. The results were even less promising when human bone marrow was employed. The human cells generally adhered to the bottom and sides of the culture vessel and their removal was difficult.

Subsequent efforts focused on inoculating mouse bone marrow onto preestablished monolayers of bone marrow stromal cells (so-called Dexter cultures; Dexter, *Acta Haematol,* 62:299–305, 1979). While some success was obtained with Dexter cultures of mouse cells, the same approach was disappointing with human cells, in that a steady decline in the numbers of all cell types is observed in human Dexter cultures (Quesenberry, *Curr. Topics Microbiol. Immunol.* 177: 151 (1992)).

A further disadvantage of Dexter cultures is that to the extent that there is expansion of hematopoietic precursor cells, these cells adhere to the stromal layer and are extremely difficult to recover from the culture without employing conditions which damage the cells. The proliferating cells which are released into the culture medium (that is, the non-adherent cells) are generally more mature cells, which cannot restore sustained hematopoiesis in a transplanted individual.

There remains a need in the art for a method of culturing human hematopoietic cells, which method (a) results in expansion of the number of hematopoietic precursor cells; (b) enhances the yield and recovery of the precursor cells without compromising viability; and (c) can be independent of the presence of bone marrow stromal elements. Quite surprisingly, the present invention fulfills this and other related needs.

SUMMARY OF THE INVENTION

The present invention provides methods and compositions for sustaining and/or expanding the number of human hematopoietic precursor cells. In one embodiment the method for sustaining or expanding the human hematopoietic precursor cells includes inoculating the cells from a blood product, such as bone marrow, umbilical cord blood, or peripheral blood, into a culture vessel which contains a culture medium that has been conditioned by exposure to a human stromal cell line. A preferred human stromal cell line secretes at least LIF, KL, MIP1$\alpha$, and IL-6, and is exemplified by the human stromal cell line designated HS-5. The conditioned culture medium of the invention may be supplemented with at least one exogenously added growth factor, such as, for example, granulocyte colony stimulating factor, stem cell factor, interleukin-3, PIXY-321 (GM-CSF/IL-3 fusion), etc. The hematopoietic precursor cells are optionally separated from mature hematopoietic cells present initially in the blood product prior to inoculating the conditioned culture medium. Further, the separated hematopoietic precursor cells may be frozen initially for storage, and then thawed prior to inoculating the conditioned medium. Typically the cells will be cultured for a time and under conditions sufficient to achieve at least an approximately two- to five-fold expansion in the number of precursor cells relative to the number of cells present initially in the blood product. After the desired expansion or maintenance has taken place, the human hematopoietic precursor cells can then be harvested from the culture medium and returned to a patient, or frozen and stored.

In other aspects the invention provides compositions for sustaining or expanding the number of human hematopoietic precursor cells. In one embodiment the composition comprises a nutrient medium that has been conditioned by exposure to an immortalized human stromal cell line, such as the HS-5 line. The composition may also be supplemented with at least one exogenously supplied growth factor, such as granulocyte colony stimulating factor, stem cell factor, interleukin-3 or PIXY-321, etc. In other embodiments the invention provides an immortalized human stromal cell line which sustains the proliferation of human hematopoietic precursor cells. Preferred lines produce cytokines such as LIF, XL, MIP1$\alpha$ and IL-6, as exemplified by the preferred line, HS-5.

The immortalized human stromal cell lines of the invention can also be used as feeder layers in ex vivo bone marrow cultures or in colony forming assays, such as the methylcellulose assay for CFU-GM. Alternatively, the cell lines of the instant invention may be used to condition medium, which medium may then be used to sustain and/or expand ex vivo cultures of human hematopoietic precursor cells, or to sustain colony forming assays. In a further aspect of the invention, medium conditioned by exposure to the immortalized human stromal cell lines may also be used in vivo to promote hematopoiesis in patients whose bone marrow function is compromised.

BRIEF DESCRIPTION OF THE FIGURES

FIG. 3 shows the number of hematopoietic colonies grown from $38^+$ or $38^{lo}$ cells in the presence of GF mix, HS-5 conditioned medium, HS-21 conditioned medium with serum (s) or serum deprived (sd).

DESCRIPTION OF THE SPECIFIC EMBODIMENTS

Figure 1A:
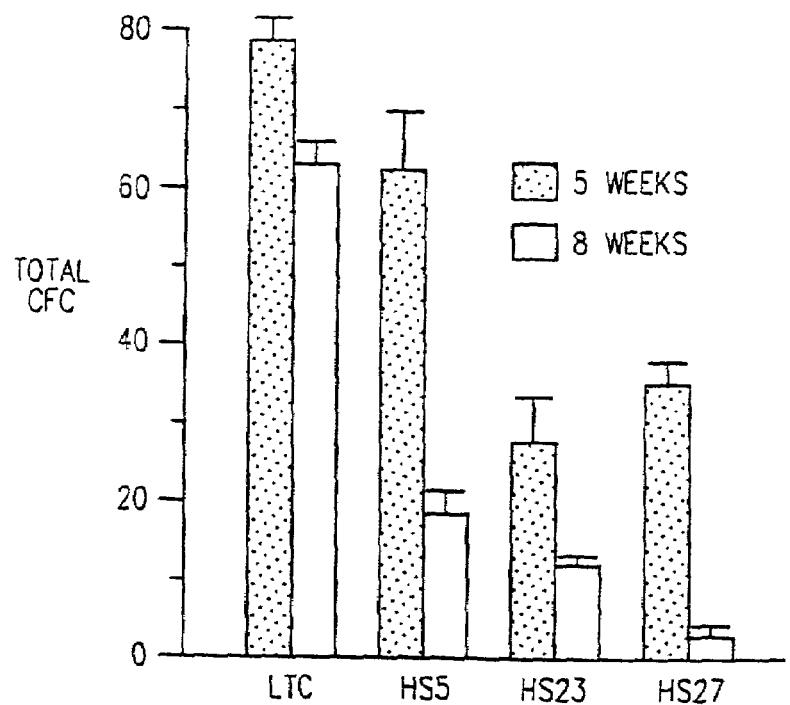
FIG. 1 shows the results of two experiments that represent the range of CFC production by primary LTC and the stromal cell lines HS-5, 23, 27 in FIG. 1A and HS-5, 21, and 27 in FIG. 1B. N=3 for FIG. 1A, and N=4 for FIG. 1B. Data are reported as the mean of the absolute number of CFC produced from adherent and non-adherent layers in replicate cultures that were initiated with 1500 $38^{lo}$ cells. Error bars represent S.E.M.
Figure 1B:
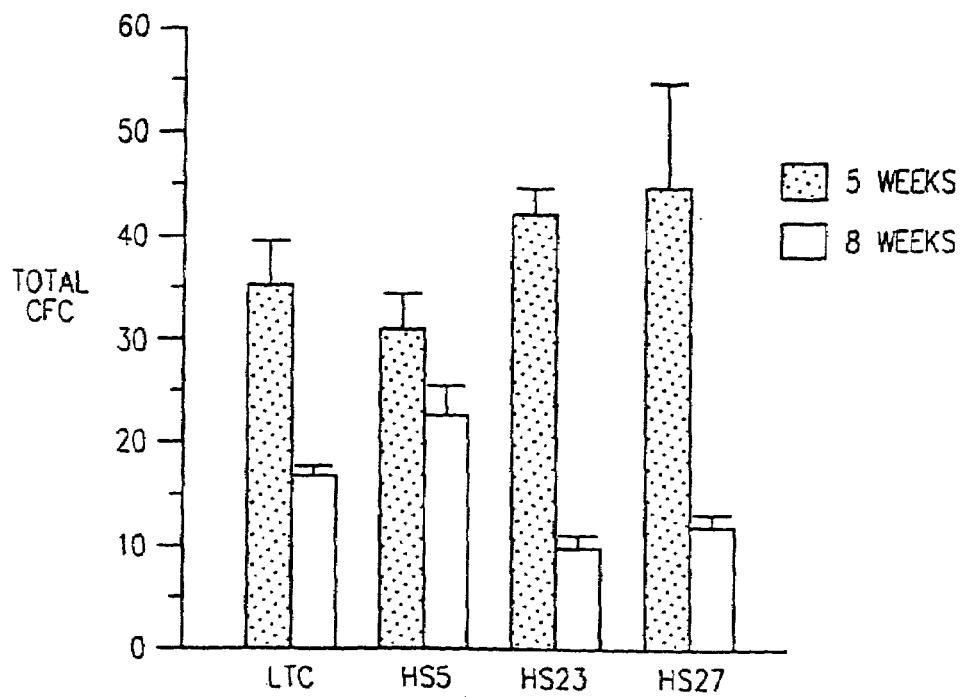

The present invention provides compositions and methods for increasing the number of human hematopoietic precursor cells in vitro and in vivo. Specifically, the present invention provides immortalized human stromal cell lines that can be used as feeder layers to sustain the growth and differentiation of human hematopoietic precursor cells ex vivo. In another aspect, the immortalized human stromal cell lines of the present invention can be used to condition medium, which medium can be used in addition to or in lieu of a feeder cell layer and/or exogenously added growth factors to support the growth of human hematopoietic precursor cells.

Human hematopoietic precursor cells are separated from a blood product, such as bone marrow, peripheral blood, or umbilical cord blood of a patient or donor, fetal peripheral blood and other sources. As discussed in more detail below, such separation may be performed, for example, by immunoselection on the basis of their expression of an antigen, such as the CD34 antigen, which is present on substantially all hematopoietic precursor cells, but is substantially absent from more mature hematopoietic cells. The separated hematopoietic precursor cells may be stored frozen and thawed at a later date for inoculation into a suitable vessel containing a culture medium comprising a conditioned medium and nutritive medium, optionally supplemented with a source of growth factors, and, optionally, human or other animal plasma or serum. Alternatively, the separated cells may be inoculated directly into culture without first freezing. In both cases the resultant cell suspension is cultured under conditions and for a time sufficient to increase the number of hematopoietic precursor cells relative to the number of such cells present initially in the blood product. The cells may then be separated by any of a variety of methods, such as centrifugation or filtration, from the medium in which they have been cultured, and may be washed one or more times with fresh medium or buffer. Optionally, the cells may be re-separated into CD34-positive and -negative fractions, prior to resuspension to a desired concentration in a medium or buffer suitable for infusion. The cells may then be infused into a patient or stored frozen for infusion at a later date.

Surprisingly, separated precursor cells, such as CD34-positive cells, will expand in number when cultured in the presence of conditioned medium containing expressed products of bone marrow stromal elements, enabling clinically practicable expansion and recovery of hematopoietic precursor cells. By working with separated precursor cells, the volumes of cells and culture fluids which must be handled are reduced to more manageable numbers. Further, a high degree of expansion can be achieved when one starts with separated CD34-positive cells, rather than with an unseparated blood product. This is believed to be due to the removal of cells otherwise present in the blood product, which inhibit expansion of the precursor cells. Under the conditions employed in the methods of this invention, cell recovery is greatly facilitated and viability is preserved. Most importantly, the yield of hematopoietic precursor cells, capable of mediating both long-term and short-term hematopoietic recovery in a myelosuppressed or myeloablated host, is increased. The ability to sustain or expand hematopoietic precursor cells in vitro or in vivo by the compositions and methods of the present invention is expected to have tremendously important consequences for disease treatments which are inherently myelosuppressive or myeloablative, such as in cancer chemotherapy.

Within the context of the present invention, hematopoietic precursor cells include those cells which express the CD34 antigen, among other surface antigens, and include totipotent stem cells as well as committed progenitor cells. The level of expression of the CD34 antigen will vary from one cell type to another. Consequently, a cell is operationally defined as CD34-positive if it expresses sufficient CD34 antigen to be detected by a given method of assay. For example, CD34-positive cells can be identified by flow microfluorimetry using a fluorescence-activated cell sorter (FACS), by immunofluorescence or immunoperoxidase staining using a fluorescence or light microscope, by radioimmunoassay, or by immunoaffinity chromatography, among numerous other methods which will be readily apparent to one skilled in the art (see, for example, Lansdorp and Thomas (in *Bone Marrow Processing and Purging*, A. P. Gee (ed.), Boca Raton: CRC Press (1991) pg. 351). Hematopoietic precursor cells can also be detected by various colony-forming assays, such as CFU-GM and CFU-S assays (see, e.g., Sutherland et al., in *Bone Marrow Processing and Purging*, supra at p. 155).

Hematopoietic precursor cells, including CD34-positive cells, may be obtained from any of a variety of blood products, including bone marrow, peripheral blood, umbilical cord blood, fetal liver, and spleen. Bone marrow is a particularly rich source of precursor cells (1–2% of marrow), but alternate sources may be preferable because of the discomfort associated with bone marrow aspiration. Bone marrow is typically aspirated from the iliac crest, but may be obtained from other sites (such as the sternum or vertebral bodies) if necessitated by prior or concurrent disease or therapy.

Peripheral blood contains fewer precursor cells (typically <1% of peripheral blood mononuclear cells), but is generally easier to obtain than bone marrow. The number of precursor cells circulating in peripheral blood can be increased by prior exposure of the donor to certain growth factors, such as, for example, G-CSF or SCF (KL), and/or certain drugs, such as, for example, 5-fluorouracil, cyclophosphamide or prednisone (Korbling and Martin, *Plasma Ther. Transfer Technol.* 9:119 (1980)). Peripheral blood collected from patients or donors who have been pretreated to increase the number of circulating CD34-positive cells is referred to as having been "mobilized." Depending upon the volume which is desired, blood may be obtained by venipuncture or by one or more aphereses, for example, on a COBE 2997 blood separator. Precursor cells can also be obtained from umbilical cord blood at the time of delivery, either by simple gravity-induced drainage or manual expression as described in U.S. Pat. No. 5,004,681, incorporated herein by reference.

Although one can readily separate a bone marrow or peripheral blood specimen or apheresis product into precursor and mature cells, (such as CD34-positive and CD34-negative populations), it is generally preferred to prepare a buffy coat or mononuclear cell fraction from these specimens first, prior to separation into the respective populations. Methods for the preparation of buffy coats and mononuclear cell fractions are well-known in the art (Kumar and Lykke, *Pathology* 16:53 (1984)).

Separation of precursor cells from more mature cells can be accomplished by any of a variety of methods known to those skilled in the art, including immunoaffinity chromatography (Basch et al., *J. Immunol. Methods* 56:269 (1983)), fluorescence-activated cell sorting, panning (wysocki and Sato, *Proc. Natl. Acad. Sci. USA* 15: 2844 (1978)), magnetic-activated cell sorting (Miltenyi et al., *Cytometry* 11: 231 (1990)), and cytolysis. Generally, separation of a heterogeneous population of cells, such as in a bone marrow aspirate or a peripheral blood specimen or apheresis product, into target (such as, CD34-positive) and non-target (such as, CD34-negative) fractions is rarely complete. For the purposes of the present invention, separation is considered to have been accomplished if the target fraction is comprised of at least about 20% precursor cells, more often about 50% precursor cells, and preferably about 70% precursor cells. In addition, it may be desirable to keep the total numbers of mature hematopoietic cells, such as platelets, granulocytes, and red cells, as low as possible in order to prevent clumping and the release of degradative enzymes which can adversely affect the recovery and viability of engrafting cells, especially after freezing and thawing. More specifically, it may be desirable that the target fraction be comprised of less than about 5% platelets, 50% granulocytes, and 10% red cells and, preferably, less than about it platelets, 25% granulocytes, and 1% red cells.

Precursor cells may be positively selected or negatively selected. By positive selection is meant the capture of cells by some means, usually immunological, on the basis of their expression of a specific characteristic or set of characteristics (usually an antigen(s) expressed at the cell surface). For example, CD34-positive cells can be positively selected by any of the above methods (except cytolysis, which would result in destruction of the desired cells) on the basis of their expression of the CD34 antigen utilizing an anti-CD34 antibody, such as the monoclonal antibodies 12.8, My-10, and 8G12 (commercially available from Becton Dickinson Co., Mountain View, Calif.), or Q-Bend 10 (commercially available from Biosystems Ltd., Waterbeach, Cambridge, England).

Negative selection means the exclusion or depletion of cells by some means, usually immunological, on the basis of their lack of expression of a specific characteristic or set of characteristics (again, usually a surface antigen). For example, CD34-positive cells can be negatively selected by any of the above methods on the basis of their lack of expression of lineage-defining antigens, such as CD 19 (for B lymphocytes), CD3 (for T lymphocytes), CD56 (for NK cells), etc., utilizing antibodies to the above-mentioned and other lineage-defining antigens. By using a cocktail or mixture of monoclonal antibodies directed to red cell, platelet, granulocyte, lymphocyte and/or tumor cell antigens, it is possible to leave behind a population of cells which is highly enriched for CD34-positive cells. Numerous monoclonal and polyclonal antibodies suitable for this purpose are known in the art (see Leukocyte Typing IV, Knopp et al. (eds.), Oxford UP, 1989) and are commercially available from a wide variety of sources (for example, Becton Dickinson Co., Mountain view, Calif.; Coulter Immunology, Hialeah, Fla.; Ortho Diagnostics, Raritan, N.J., etc.).

Alternatively, precursor cells can be separated from mature cells by a combination of negative and positive selection techniques. A preferred combination of negative and positive selection techniques is comprised of a first selection for CD34-positive cells utilizing an anti-CD34 antibody, followed by a second selection for HLA-DR-negative/CD34-positive cells, using an anti-HLA-DR antibody to a non-polymorphic determinant on the DR molecule. Antibodies to non-polymorphic determinants on the HLA-DR molecules are well-known in the literature (see Knopp et al., supra) and are available from a variety of sources, including those mentioned above. An example of a suitable monoclonal anti-HLA-DR antibody is the antibody produced by the hybrid cell line L243 (Lampson et al., *J. Immunol.* 125: 293 (1980)), which cell line is available from the American Type Culture Collection (Rockville, Md.) under the designation ATCC HB55. The advantage of this or other dual selection strategies is that the volume of cells which is placed into culture is smaller and thus more manageable.

Although selection of CD34-positive cells usually involves the use of one or more antibodies or fragments thereof, in some cases selection may involve the use of lectins or other types of receptors or ligands expressed on the cell surface. Among other antibodies, antigens, receptors and ligands which may be useful, alone or in combination with other markers, for separating CD34-positive cells from CD34-negative cells are transferrin, the transferrin receptor, soybean agglutinin, c-kit ligand, c-kit receptor, HLA-DR, CD33, etc.

Within another aspect of the invention, the precursor cells are periodically separated from more mature cells. Briefly, mature cells (which include not only terminally differentiated blood cells, but cells of an intermediate lineage) may inhibit the expansion and differentiation of precursor cells via a feedback control mechanism. Removal of more mature cells from a culture thus permits expansion of the precursor cells to many times their original numbers. Within the context of the present invention, "periodically separating" means removal of mature cells at least every 7 days, preferably every 4 days.

Various methods may be utilized in order to periodically separate precursor from mature cells. For example, cells can be separated on an affinity column, incubated in a selected medium, and then subsequently reseparated in order to separate the precursor cells from the newly differentiated mature cells. Particularly preferred methods and devices for the selection of precursor cells, such as CD34-positive cells, are described in U.S. Pat. Nos. 5,215,927, 5,225,353, 5,262,334 and 5,240,856, each of which is incorporated herein by reference in its entirety. These applications describe methods and devices for isolating or separating target cells, such as hematopoietic precursor cells, from a mixture of non-target and target cells, wherein the target cells are labeled, directly or indirectly, with a biotinylated antibody to a target cell surface antigen. Labeled cells are separated from unlabeled cells by, flowing them through a bed of immobilized avidin, the labeled cells binding to the avidin by virtue of the biotinylated antibody bound to their surface, while the unlabeled cells pass through the bed. After washing the bed material, the labeled (bound) cells can be eluted from the bed, for example, by mechanical agitation. A cell-separator device is also provided for separating target cells from non-target cells, comprising (a) a column assembly which includes a column, a sample fluid supply bag and a fluid collection bag wherein the column is provided for receiving the sample fluid from the sample fluid supply bag and for separating the target cells from the sample fluid and retaining the target cells, and wherein the fluid collection bag is provided for receiving the target cells after being released from the column, (b) an agitation means for agitating the contents of the column to assist in releasing the sample cells retained in the column, the agitation means being responsive to a drive signal for varying amounts of agitation of the contents of the column to vary the rate at which the sample cells are released, (c) a column sensor means for providing a column signal indicative of the optical density of fluid flowing out of the column and into the fluid collection bag, (d) a column valve means responsive to a column valve control signal for selectively enabling the fluid coming out of the column to flow into the fluid collection bag, and (e) a data processor means for controlling the operation of the cell separator, the data processor means being responsive to the column signal for providing the drive signal and the column valve control signal to prevent inadequate concentrations of the target cells from being collected. One embodiment of this invention is the CEPRATE SC™ cell separation system described in Berenson et al. (*Adv. Bone Marrow Purging & Processings,* N.Y.: Wiley-Liss, 1992, pg. 449).

Subsequent to separation, precursor cells are inoculated into a culture medium comprised of a nutritive medium, any number of which, such as RPMI, TC 199, Ex Vivo-10, or Iscove's DMEM, along with a source of growth factors, will be apparent to one skilled in the art. Proliferation and differentiation of precursor cells may be enhanced by the addition of various components to the medium, including a source of plasma or serum. Among sources of plasma or serum are fetal bovine and human. Particularly preferred are human autologous plasma or human AB$^-$ plasma which have been screened in accordance with standard blood bank procedures to ensure the absence of infectious agents, such as HBV or HIV. The amount of plasma or serum which is used will vary, but is usually between about 1 and 50% (by volume) of the medium in which the cells are grown, and more often between about 1 and 25%.

According to one aspect of the present invention, separated precursor cells are cultured in a nutritive medium containing a source of plasma or serum, which medium has been previously conditioned by exposure to immortalized stromal cells for a variable period of time and under conditions sufficient to allow those cells to secrete products, such as growth factors, into the medium. For example, conditioned medium suitable for the culture of separated CD34-positive cells may be prepared by inoculating an immortalized stromal cell line HS-5 as described herein into a nutrient medium (optionally containing plasma or serum), allowing the cells to grow, usually for 1 to 3 days, and then separating the cells from the medium (for example, by centrifugation or filtration). Optionally, the conditioned medium may be sterilized and/or concentrated prior to use and/or supplemented by the addition of exogenous growth factors.

Although the HS-5 stromal cell line is particularly preferred for generating conditioned medium, other cell lines can be prepared and selected according to the present invention which secrete a variety of growth factors and which may be used to prepare the conditioned medium for short term or long term support of hematopoiesis. Typically, such cell lines are prepared by transfecting a long term marrow culture with a retroviral supernatant, the retrovirus carrying an oncogene, integration of which leads to immortalization of the transfected cell and its progeny. The retroviral vector may also carry a gene for a selectable marker, such as neomycin resistance, to facilitate identification of transfected cells. Following transfection, cells are cloned and characterized morphologically and histochemically, as well as functionally to ascertain their ability to sustain hematopoiesis ex vivo. Growth factors expressed by the resultant cell lines can be assayed, for example, by ELISA or RIA.

In addition, it will be apparent that in some instances it may be desirable to inoculate multiple cell lines simultaneously to produce medium conditioned by more than one line. Alternatively, different batches of medium can be conditioned by different cell lines and the batches combined, after the cells have been separated and discarded, to achieve the same effect.

The length of time for which medium is conditioned may vary from 1 day to 2 weeks, but will usually be between 1 day and 1 week and more often, between 1 day and 5 days. In addition to conditioning the medium by exposing it to immortalized stromal cells such as the HS-5 cell line, the medium may also be supplemented by the addition of one or more purified or partially purified growth factors, such as those mentioned above. The term "conditioned medium" is used to include medium conditioned solely by exposure to cells as well as medium conditioned by exposure to cells and supplemented with exogenous growth factors.

Conditioned medium may be prepared with or without a source of serum or plasma. If used, the serum or plasma may be of human or other animal origin. Particularly preferred is human autologous plasma or human AB$^-$ plasma which has been screened in accordance with standard blood bank procedures to ensure the absence of infectious agents. The amount of plasma or serum which is used will vary, but is usually between about 1 and 50% (by volume) of the medium in which the cells are grown, and more often between about 1 and 25%.

The conditioned medium of the present invention may be concentrated prior to use by a variety of means, for example, by ultrafiltration, although other concentrating means will also suffice. The amount of concentration will vary, but is usually between 2 and 100-fold, more often between 2 and 50-fold, and most often between 2 and 10-fold. Separated precursor cells may be inoculated directly into conditioned medium (concentrated or non-concentrated) or they may be inoculated into a mixture of conditioned (concentrated or non-concentrated) and non-conditioned medium (with or without exogenously supplied growth factors and serum or plasma). If inoculated into a mixture of conditioned and non-conditioned medium, the ratio of conditioned (non-concentrated) to non-conditioned medium will usually be between 1:1 and 1:10 (on a volume basis), more often between 1:1 and 1:5, and most often between 1:1 and 1:2. Although these ratios are expressed for non-concentrated conditioned medium, it will be apparent to those skilled in the art that the equivalent ratios can be obtained using smaller volumes of concentrated conditioned medium.

Among growth factors which may be advantageously employed in the medium are interleukins (IL) 1–15, erythropoietin (EPO; U.S. Pat. No. 4,703,008, incorporated herein by reference), stem cell factor (SCF, also known as mast cell growth factor and c-kit ligand), granulocyte colony stimulating factor (G-CSF), granulocyte, macrophage-colony stimulating factor (GM-CSF), macrophage-colony stimulating factor (M-CSF), transforming growth factor beta (TGF beta), tumor necrosis factor alpha (TNF alpha), the interferons (IFN alpha, beta, or gamma), fibroblast growth factor (FGF), platelet-derived growth factor (PDGF), insulin-like growth factors (IGF-1 and IGF-2), megakaryocyte promoting ligand (MPL) and SLK-2, etc. Growth factors are commercially available, for example, from R&D Systems (Minneapolis, Minn.). Particularly preferred are combinations of growth factors, especially the combination of SCF, IL-1 alpha, IL-3 (EP Publ. EP 275,598 and 282,185, incorporated herein by reference) and IL-6. It may also be desirable to selectively remove inhibitors of hematopoiesis, as described in, e.g., Maxwell et al., using an antibody, soluble receptor or the like.

In general, the above-mentioned growth factors are purified or partially purified before they are added to the culture medium. Usually, they will be produced by recombinant DNA methods, but they may also be purified by standard biochemical techniques from conditioned media. Non-naturally-occurring growth factors can also be produced by recombinant DNA methods, for example, PIXY-321 is a fusion protein which has both GM-CSF and IL-3 activity, as described in U.S. Pat. No. 5,108,910, incorporated herein by reference. It will be evident to those skilled in the art that other fusion proteins, combining multiple growth factor activities, can be readily constructed, for example, fusion proteins combining SCF activity with that of other growth factors such as IL-1, IL-3, IL-6, G-CSF, and/or GM-CSF.

The amount of each growth factor to be used is determined empirically and will vary depending on the purity and method of production of the factors. Generally, concentrations between 0.5 and 100 ng/ml are sufficient, more often between 0.5 and 50 ng/ml. Where more than one growth factor is used, the optimum amount of each factor should be determined in combination with the other factors to be used. This is because some growth factors can modulate the activity of other growth factors, necessitating that they be used sequentially rather than simultaneously, while in other instances, growth factors may act synergistically. Still other growth factors may enhance proliferation or differentiation along one pathway, while suppressing another pathway of interest.

Separated precursor cells may be cultured in any vessel which is capable of being sterilized, is adapted or adaptable to gas exchange with the atmosphere, and is constructed of a material which is non-toxic to cells. A variety of vessels suitable for this purpose are well-known in the art, including stirring flasks (Corning, Inc., Corning, N.Y.), stirred tank reactors (Verax, Lebanon, N.H.), airlift reactors, suspension cell retention reactors, cell adsorption reactors,.and cell entrapment reactors, petri dishes, multiwell plates, flasks, bags and hollow fiber devices. If agitation is desired, it can be attained by any of a variety of means, including stirring, shaking, airlift, or end-over-end rotation. In addition to maintaining the culture in suspension by agitating the medium (as by stirring or airlift), the culture can also be maintained in suspension by matching the density of the culture medium to the density of the cells or microcarrier beads.

The immortalized human stromal cell lines of the instant invention can be used as feeder layers in ex vivo bone marrow cultures or in colony forming assays, such as the methylcellulose assay for CFU-GM or the cobblestone area forming cell (CAFC) assay. Alternatively, the cell lines of the instant invention may be used to condition medium, which medium may then be used to sustain and/or expand ex vivo cultures of human hematopoietic precursor cells, or to sustain colony forming assays, such as the CFU-GM and CAFC assays. For example, methylcellulose assays are typically performed using conditioned medium from lymphocytes stimulated with the lectin phytohemagglutinin (PHA-LCM). Human stromal cell line conditioned medium (HS-CM) can be substituted for PHA-LCM in methylcellulose assays. Medium conditioned by exposure to the immortalized human stromal cell lines may also be used in vivo to promote hematopoiesis in patients whose bone marrow function is compromised.

The following examples are offered by way of illustration, not by way of limitation.

EXAMPLE I

Production of Human Stromal Cell Lines

This Example describes the production and characterization of HPV 16 E6/E7 immortalized human marrow stromal cell clones. In subsequent Examples the stromal cell clones are shown to support the proliferation of hematopoietic progenitors and maintain colony forming cells (CFC) for up to 8 weeks in culture.

Adult bone marrow was obtained from normal donors and LTMC (long term marrow cultures) were established as described by Gartner and Kaplan, *Blood* 56:117 (1980). Briefly, buffy coat cells from marrow aspirates were plated in plastic tissue culture dishes at $1-2 \times 10^6$ cells per ml. Adherent cells were grown in Long term culture (LTC) medium containing Iscoves, 12.5% horse serum, 12.5% fetal calf serum, L-glutamine (0.4 mg/mL), sodium pyruvate (1 mM), penicillin (100 U/mL), streptomycin sulfate (100 µg/mL), hydrocortisone sodium succinate ($10^{-6}$ M) and β-mercaptoethanol ($10^{-4}$M).

For immortalization of bone marrow cells lines, the LTMCs were infected with the amphitrophic LXSN-16 E6/E7 retrovirus that was packaged in the PA317 cell line as described in Halbert et al., *J. Virol.* 65:473 (1991), incorporated herein by reference. Primary LTMC were exposed to virus in the presence of 4 µg/ml polybrene (Aldrich Chemical Co. Inc., Milwaukee, Wis.) for 2 hours at 37° C. The virus containing medium was removed and the cells were incubated for an additional 5 hours with medium containing polybrene. Cells were then washed and fed with LTC medium and incubated an additional 48 hours. Cell cultures were then trypsinized and replated at limiting dilution. Transduced clones were selected with 50 µg/ml G418 and resistant colonies were picked and grown in LTC medium using standard tissue culture techniques. Following expansion most clones were switched to RPMI containing 10% serum and HS-5 was switched to serum deprived medium containing 1% Nutridoma (Boehringer-Mannheim), 100 mM glutamine, 100 mM sodium pyruvate, 100 U/mL penicillin-streptomycin in Iscoves media.

Twenty-seven foci were identified and isolated using cloning rings to establish stromal cell lines (HS-1 to HS-27) of which twenty-four were retained and proved to be resistant to G418 at 50 µg/ml. All lines were initially characterized morphologically and histochemically, screened for maintenance and/or proliferation of HPs (see below) and then frozen. Several clones designated HS-5, HS-21, HS-23 and HS-27 were selected for more detailed analysis and have been maintained in continuous culture for up to 20 months with periodic analysis of their phenotypes.

Based on morphology two distinct cell types were observed, small fibroblastic (HS-5, HS-21) and large flattened epithelioid (HS-23, HS-27). The two fibroblastic lines, although similar in morphology, differed in regard to growth patterns. HS-5 formed a reticulum of overlapping cells, reminiscent of astrocytes, whereas HS-21 cells were well separated and lined up in parallel arrays. At higher densities HS-5 formed a dense "net" of cells, whereas HS-21 formed a contiguous monolayer with discernible cell boundaries. HS-23 and HS-27 formed large flattened polygonal shaped cells that exemplify "blanket" cells and maintain numerous intercellular contacts with neighboring cells. HS-23 and -27 also formed monolayers, however because of their flattened morphology it was difficult to identify distinct cell boundaries.

Southern hybridization on genomic DNA from the 4 cell lines was used first to confirm that LXSN-16 E6/E7 had integrated, and second to establish clonality. Genomic DNA was isolated from $1 \times 10^7$ stromal cells using a modification of the technique described in Ausebel et al., (eds.) *Current Protocols In Molecular Biology*, New York, Wiley Interscience (1987). Prior to southern hybridization 10 µg of genomic DNA was digested with excess EcoRI overnight at 37° C. The DNA was extracted with phenol:chloroform and precipitated. The digested genomic DNA (10 µg) was separated on a 0.5% agarose gel in TBE and then transferred to a nylon membrane according to manufacturers specifications (Hybond, Amersham). The membrane was hybridized with random primed probes generated against the E6E7 insert. 50,000 cpm was hybridized overnight at 42° C. and washed 2× with 2×SSPE at 25° C. and then washed 2 more times with 0.2×SSPE containing 0.1% SDS at 60° C. prior to autoradiography. The autoradiographs indicated that all cell lines contained retroviral insert(s) with only a single band present in HS-5 and HS-23. However HS-21 and HS-27 had two bands, indicating either that they contained two inserts or that two clones contribute to the line. Analysis of foreskin fibroblasts and plasmid DNA indicated that the probe was specific for the LXSN 16 E6/E7 integrant.

The antigenic phenotypes of the stromal cell lines were then determined by routine immunochemistry procedures using a variety of markers. The following antigens were identified with available monoclonal antibodies: Smooth muscle actin (monoclonal antibody IA4-IgG2a; Sigma); CD14 (monoclonal antibody leuM3-IgG2b, Becton-Dickinson) was used as a marker for macrophages; FVIII antigen (human type 1) was identified with monoclonal antibody obtained from Calbiochem, La Jolla, Calif.) as a marker for endothelial cells; Monoclonal antibody 6.19-IgG2a was used to identify fibroblasts, endothelial cells and adipocytes (obtained from C. Frantz, University of Rochester School of Medicine and Dentistry, Rochester N.Y.); CD34 was identified with monoclonal antibody 12.8 (IgM, I. Bernstein, Fred Hutchinson Cancer Research Center [FHCRC]); fibronectin and vimentin were identified with monoclonal antibody P1H11 and P1H1-C9, respectively (obtained from W. Carter, FHCRC); Class I MHC antigen was identified with monoclonal antibody 60.5, (P. Martin, FHCRC); VLA-4 and VCAM-1 were identified with monoclonal antibodies (4B9 ascites, J. Harlan, Univ. Washington); collagen Type I was identified with MAB1340 (IgG), Type III was identified with MAB1343 (IgG1), and Type IV was identified with MAB 1910 (IgG1), each obtained from Chemicon, Temecula Calif. Similar monoclonal antibodies can be readily obtained and substituted for those used in this study to identify the cellular antigens of interest.

For immunofluorescence staining, semi-confluent cells were rinsed with warm HBSS and fixed for 10 minutes with 1% formaldehyde in PBS at 25° C. The cells were washed with phosphate buffered saline (PBS) and treated with 0.2 M glycine in PBS for 5 minutes at 25° C. One additional wash was performed with PBS prior to incubation with a specific antibody or irrelevant non-specific isotype control antibody for 1 hr at 25° C. After incubation with the primary antibody the cells were washed 3× and incubated with a secondary antibody (goat anti-mouse IgG/IgM fluorescein isothiocyanate (FITC)-conjugated antibody (Tago) for 1 hr at 25° C. and washed with PBS prior to viewing with a Nikon Diaphot fluorescent microscope. Primary LTCs and foreskin fibroblasts (FSF) were used as controls for antibody staining.

The results of the indirect immunofluorescence, shown in Table 1, indicated that all cell lines were negative for MHC Class II (DR) and CD14, a macrophage specific marker, and positive for antigens normally associated with non-hematopoietic stromal cells. All lines expressed collagen III and IV, with low levels of collagen I detected on HS-5 and HS-27. Analysis of VCAM-1 revealed that HS-5 and HS-21 expressed low levels, HS-23 was heterogeneously positive, and HS-27 was homogeneously a strong positive.

TABLE 1

| | | Stromal Cell Lines | | | |
|---|---|---|---|---|---|
| Markers | MoAB | HS-5 | HS-21 | HS-23 | HS-27 |
| Smooth Muscle Actin | IA4 | +++ | +++ | +++ | +++ |
| MHC Class I | 60.5 | +++ | ++ | ++ | ++ |
| MHC Class II | P4.1 | − | − | − | − |
| Fibroblasts, Adipocytes Endothelial cells | 6.19 | ++ | ++ | ++ | ++ |
| FVIII Agn | | − | − | − | − |
| Macrophage (CD14) | leuM3 | − | − | − | − |
| Endopeptidase (CD10) | J5 | +++ | + | + | + |
| Fibronectin | P1H11 | ++ | ++ | ++ | ++ |
| CD34 | 12.8 | − | − | − | − |
| Stromal, Endothelial | STRO-1 | − | − | − | − |
| Mesenchymal (Vimentin) | P1H1-c9 | + | + | + | + |
| Collagen I | MAB1340 | + | − | − | + |
| Collagen III | MAB1343 | +++ | + | +++ | ++ |
| Collagen IV | MAB1910 | +++ | + | ++++ | ++ |
| VCAM-1 | 4B9 | + | + | ++/− | +++ |

TABLE 1-continued

| | | Stromal Cell Lines | | | |
|---|---|---|---|---|---|
| Markers | MoAB | HS-5 | HS-21 | HS-23 | HS-27 |
| Alkaline Phosphatase | | − | +/− | +/− | +/− |
| Acid Phosphatase | | +++ | + | +++ | ++ |

Indirect-immunofluroescent and cytochemical analysis of the stromal cell lines. +/− indicates that the cell lines were heterogeneously positive and − represents the lack of detectable antigen. ++ indicates good staining and +++ indicates that the cells were strongly positive.

Cytochemical analysis for alkaline phosphatase activity was determined using cells fixed with 2% formaldehyde in absolute methanol for 30 seconds at 4° C. (35), then washed with distilled water and air dried. After drying the cells were incubated at 37° C. for 30 minutes in filtered reaction buffer containing 0.2 M Tris HCl (pH 9.1), 1.0 mg/mL Fastblue BB with or without 0.2 M napthal AS phosphate in N,N-dimethylformamide. After incubation the cells were washed with distilled water, overlaid with Aqua Mount (Lerner Laboratories, Pittsburgh, Pa.) and photographed with a Nikon Diaphot microscope.

For analysis of acid phosphatase activity the cells were fixed with 60% acetone in 0.04 M citrate buffer (pH 5.4) for 30 seconds at 25° C., rinsed with distilled water, air dried and incubated with the reaction buffer. The reaction buffer was made up in 24 mls of 0.1 M acetate buffer with or without 12.5 mg Napthal AS-BI phosphate as substrate and 7.5 mg Fast Garnet GBC dye was added as counterstain. This solution was filtered through a Whatman #4 filter and then incubated with cells for 1 hour at 25° C. protected from light. After staining the cells were washed with distilled water, overlaid with Aqua-mount, photographed (Nikon Diaphot microscope) and scored for the presence of acid phosphatase.

As shown in Table 1, all lines were positive for acid phosphatase with some differences in the degree of staining. In contrast, HS-5 was negative for alkaline phosphatase staining while all others were heterogeneously positive.

The cell lines were also tested for their ability to undergo lipogenesis in response to corticosteroids. Confluent stromal lines were incubated with corticosteroids for 4 weeks and stained with oil red O to determine if these lines contain adipogenic cells as described in Kodama et al., *J. Cell Physiol*. 112: 83 (1982). Cultures were fed weekly with either dexamethasone ($10^{-7}$ M), hydrocortisone ($10^{-6}$ M), insulin (10 mg/Ml) or dexamethasone combined with insulin, in RPMI containing 10% FCS. After the incubation period the cells were washed extensively with PBS and then fixed with 10% formalin in PBS for 30 minutes. The excess formalin was washed off with PBS and the cells were stained for 15 minutes with filtered oil red O (0.3% w/v in isopropanol). The stain was then differentiated with 60% isopropanol, washed and the cells counterstained with Mayers hematoxylin for 30 seconds.

The results indicated that HS-5 and HS-21 cell lines did not accumulate lipids, whereas a few cells (approximately 1–2%) from HS-27 formed lipid vacuoles in the presence of all steroids tested. HS-23 formed lipid vacuoles in the presence of dexamethasone only. None of the lines, however acquired the large multilocular vacuoles commonly observed in adipocytes that are present in LTMCs (Gartner and Kaplan, supra, and Eaves et al., *J. Cult. Meth*. 13:55 (1991).

Thus, these stromal cell lines have increased growth rates, do not undergo senescence (some have been in continuous culture for two years), and retain characteristics of normal differentiated bone marrow stromal cells. Positive staining with monoclonal antibody 6.19 (specific for fibroblasts, endothelial and adipocytes), P4.1 (CD10, endopeptidase), P1H11 (vimentin) and the absence of a macrophage marker (CD14) indicates that the cells are mesenchymal in origin. The lack of FVIII antigen indicates that they are not endothelial, however all lines express collagen type IV which is consistent with the endothelial nature of bone marrow stroma (Novotny et al., *Exp. Hematol.* 18:775 (1990) and Zipori, in *Handbook of the Hematopoietic Microenviroment*, pp. 287–329, Ed. M. Tavassoli, Humana Press, Clifton N.J. 1989). Only the HS-23 cell line responded to dexamethasone, suggesting that it may be pre-adipocytic. The cell lines displayed a normal staining pattern for smooth muscle actin, vimentin, cell associated fibronectin and growth was inhibited at confluency. CD34 and STRO-1 were absent, which is consistent with the loss of these markers in normal bone marrow cultures after several weeks of growth (Sutherland et al., *Proc. Natl. Acad. Sci. USA* 87:3584 (1990) and Simmons and Torok-Storb, *Blood* 78: 55–62 (1991)). All 24 lines, except HS-5, were heterogeneously positive for both alkaline phosphatase and acid phosphatase.

Overall, the morphological and phenotypic characteristics of these cell lines were similar to murine bone marrow stromal cell lines (Zipori et al., *J. Cell Physiol.* 118: 143 (1984); zipori et al., *J. Cell Physiol.* 122: 81 (1985); Song et al., *Exp. Hematol.* 12: 523 (1984); and zipori, in *Handbook of the Hematopoietic Microenviroment, supra*.), SV40 transformed human cell lines (Lanotte et al., *J. Cell Sci.* 50:281 (1981); Harigaya et al., *Proc Natl. Acad. Sci. USA* 82: 3477 (1985); Tsai et al., *J. Cell Physiol.* 127: 137 (1986); Novotny et al., *Exp. Hematol.* 18: 775 (1990); Slack et al., *Blood* 75: 2319 (1990); Singer et al., *Blood* 70: 464 (1987); Cicutinni et al., *Blood* 80: 102 (1992); and Thalmeir et al., *Blood* 83: 1799 (1994)), and transient non-transformed human lines (Lanotte et al., supra). However, no spindle shaped cells were observed as others have previously reported (Novotny et al., supra) and the HPV immortalized lines remain MHC class II (DR) negative, as observed with normal marrow (Novotony, supra).

EXAMPLE 2

Stromal Lines Support Short and Long Term Hematopoiesis

A rapid screening assay was developed to demonstrate the viability and expansion of hematopoietic cells when co-cultured with the cell lines.

To isolate CD34+/38+ and 38lo cells, adult marrow was obtained from cadaveric donors. The mononuclear cells were isolated by Ficoll density centrifugation and RBCs removed by hemolysis with 150 Mm $NH_4Cl_2$ at 37° C. Marrow mononuclear cells were stored frozen in RPMI, 36% FCS, 10% DMSO, 90 U Penicillin, 90 mg/ml streptomycin sulfate, and 0.36 mg/ml glutamine. The stored cells were thawed at 37° C. and slowly diluted on ice to a final DMSO concentration below 1%. After washing, the CD34+ cells were labeled with anti-CD34 conjugated to fluorescein isothiocyanate (FITC) (HPCA-2 ($IgG_1$)) Becton-Dickinson, San Jose Calif.) for 20 minutes on ice, washed with PBS containing 1% BSA and then labeled with rat anti-mouse. $IgG_1$ conjugated to superparamagnetic microbeads (Miltenyi Biotec GmbH, Bergisch-Gladbach, Germany) (Miltenyi et al., *Cytometry* 11:231 (1990). The CD34+ cells were positively selected using High-Gradient Magnetic Cell Sorting (Miltenyi Biotec GmbH). The CD34+ enriched population was then incubated with anti-CD38 conjugated to phycoerythrin (PE) (leu-17, Becton-Dickinson) for 20 minutes on ice, washed, and sorted using a FACStar Plus (Becton-Dickenson). Cells with medium to high forward light scatter and low side scatter were selected and both the 38$^+$ and the 38$^{lo}$ population of CD34$^+$ cells were collected (Reems and Torok-Storb, *Blood,* submitted (1994)).

Both 38$^{lo}$ and 38$^+$ cells were co-cultured on stromal cell lines in serum-deprived medium for five days with and without IL-3 (10 ng/Ml) and then stained to differentiate stromal from hematopoietic cells and viable cells from dead cells. Screening was initiated by plating stromal cells at a density of 600 to a 1000 per well in Terasaki 96-well plates (Nunc) two days prior to addition of the bone marrow cells. The 38$^{hi}$ and 38$^{lo}$ cells (about 150–350 per well) were added to the cultures in serum deprived medium (Nutridoma-HU) and incubated at 37° C. in 5% $CO_2$ humidified incubator for 5 days. The viability and proliferation of progenitors was scored after the addition of 5 μl of a staining mixture which contained 2.5% India ink, 250 μg/ml ethidium bromide and 75 μg/ml acridine orange in HBSS. The number of viable cells was determined for each well by inverted fluorescence microscopy (Nikon Diaphot microscope).

All 24 cell lines maintained the viability of both 38$^+$ and 38$^{lo}$ subpopulations of CD34$^+$ cells for 5 days. When IL-3 was added to the co-cultures the 38$^+$ cells increased in number in all cases. However, cell line HS-5 was able to induce the 38$^+$ cells to proliferate without exogenous IL-3, and the addition of IL-3 to HS-5 co-culture did not increase the extent of proliferation beyond that observed with HS-5 alone. Fluorescence microscopy revealed the differences between the maintenance of 38$^+$ cells on HS-21 and the proliferation of these cells on HS-5. Small round cells were viable hematopoietic cells that accumulated acridine orange and fluoresce green, whereas large flat cells were stromal cells, and nonviable cells incorporated ethidium bromide and fluoresce orange. The same number of 38$^+$ cells were plated into each culture at the initiation of the experiment. No proliferation of 38$^{lo}$ cells was observed within the 5 day time span of this experiment.

To determine if these stromal lines could support less mature hematopoietic cells their ability to maintain or produce colony forming cells (CFC) from the 38$^{lo}$ population after 5 and 8 weeks was determined. To demonstrate long-term support of CFC, two to four week old primary LTMCs were established and maintained according to the guidelines of Gartner, supra, and Eaves, supra. Stromal cell lines were irradiated at 2000 RADS and plated into 24 well plates at least 24 hours prior to the addition of hematopoietic cells. Irradiated stromal cells were plated at sufficient cell densities to ensure formation of monolayers. The stromal cultures were seeded with 1000–3000 38$^{lo}$ cells and semidepleted weekly for 5 or 8 weeks. The non-adherent and adherent cells were harvested and analyzed for colony forming cells using methylcellulose colony assays.

Colony assays were performed using a stock solution of 1.2% methylcellulose, 2.5% BSA, 25% FCS (Hyclone 796), 100U penicillin, 100 μg/ml streptomycin sulfate, and 0.1 M β-mercaptoethanol. Colony stimulating activity was provided either by a growth factor mix containing 10 ng/ml IL-1, IL-3, IL-6, G-CSF, GM-CSF, KL and 3U/ml EPO, or by 10% conditioned media (PHA-LCM). Hematopoietic cells (38$^+$ or 38$^{lo}$) plus 100 μl growth factor mix or conditioned media was added to 0.9 mL of the methylcellulose stock. Colony formation was scored at day 14 and designations were periodically confirmed by Wright-Giemsa staining of colony cytospins.

The two representative experiments are indicative of the range of CFC production and demonstrate that the stromal lines can maintain CFC at levels comparable to primary LTMC for up to 8 weeks HS-27, which expressed the highest levels of VCAM-1, was the only cell line to establish cobblestone regions when incubated with $38^{lo}$ cells. Both the fibroblastic and "blanket" cell lines supported CFC for 5 to 8 weeks at levels comparable to primary LTC. These results indicate that independent of phenotypic differences and detectable cytokine secretion these diverse stromal cell lines produce hematopoietic maintenance factors at levels that are sufficient to support immature pluripotent progenitors.

EXAMPLE 3

Conditioned Medium Induces Hematopoiesis

Medium was conditioned by exposure to semi-confluent cultures of the immortalized human stromal cell lines for one week. Both RPMI containing 10% FCS and serum deprived (1% nutridoma-HU Boehringer Mannheim) media were used. The culture debris was pelleted by centrifugation at 2000×g for 10 minutes and the supernatant was then aliquoted and frozen at −20° C. Conditioned media was thawed only once prior to use. Concentrated conditioned medium was made using Amicon centriprep 10 concentrator (Amicon, Beverly, Mass.) according to the manufacturers specifications and protein content was determined using the BIO-RAD protein assay (Bio-Rad). Conditioned medium was assayed for colony stimulating activity in standard CFU assays and for cytokine content with ELISAs using Quantikine kits (R & D Systems, Minneapolis, Minn.) according to manufacturer's specifications. Supernatants were analyzed neat, at 1:2 and at 1:5 dilutions.

Figure 2A:
FIG. 2 shows the small-scale expansion of $38^+$ cells with growth factor mix (FIG. 2A), HS-5 conditioned medium (FIG. 2B), and HS-21 conditioned medium (FIG. 2C). The same number of cells were added per well at time zero, expanded with different media for 5 days and stained with ethidium bromide and acridine orange.
Figure 2B:
Figure 2C:
Figure 3A:
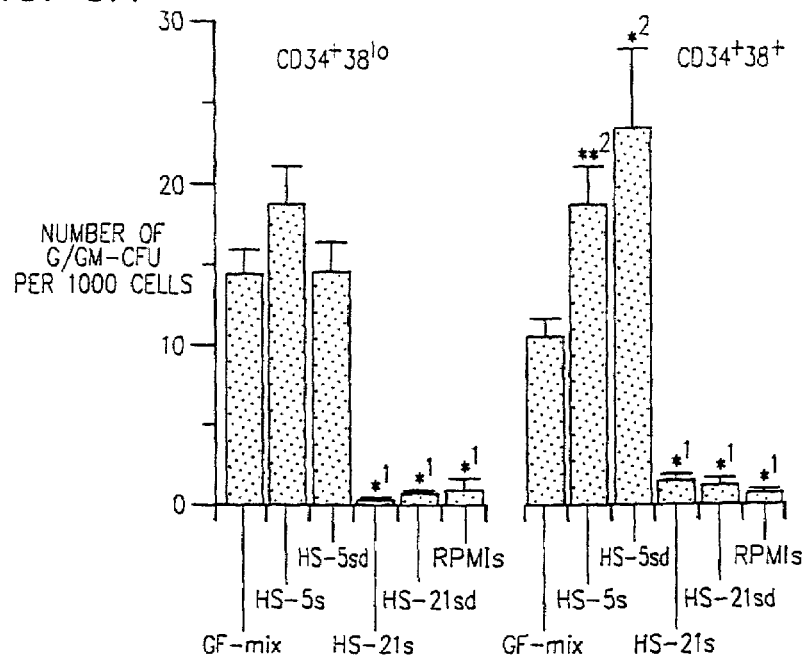
FIG. 3A shows granulocytic/monocytic colony numbers (G/GM) and FIG. 3B shows erythroid bursts (BFU-E). RPMIs represents RPMI media supplemented with 10% FCS. Results significantly different from HS-5 are designated 1, and results significantly different from GF mix are designated 2. Error bars represent S.E.M., "*" indicates P<0.01, and "**" indicates P<0.05.
Figure 3B:
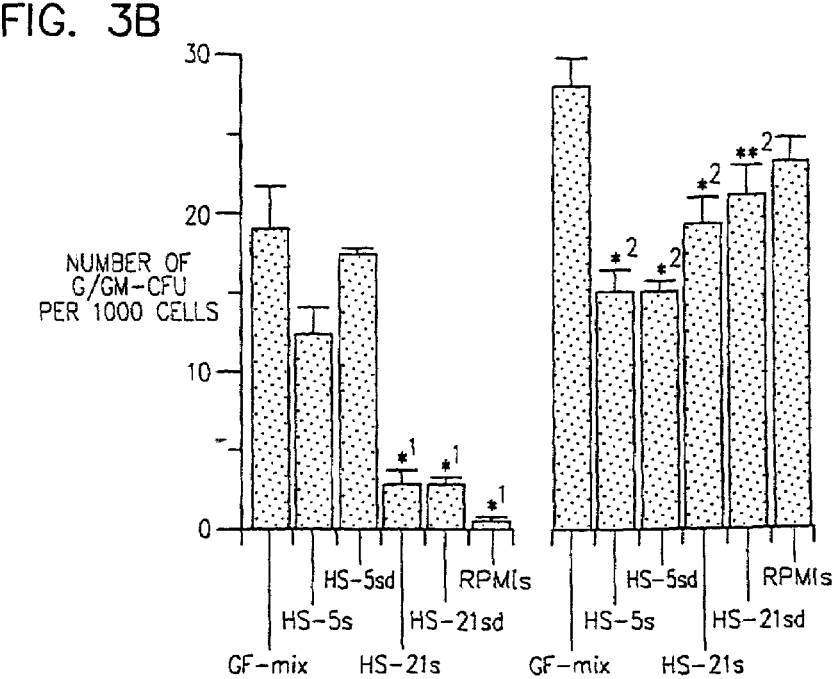

The results showed that only conditioned media from HS-5 induced proliferation of $38^+$ and $38^{lo}$ cells in the absence of stromal cells. FIGS. 2A–C demonstrate the extent of proliferation of $38^+$ cells induced by conditioned medium from HS-5 compared to conditioned medium from HS-21 and a recombinant growth factor mix. Additional experiments using concentrated HS-5 CM indicated that a 12–15 fold expansion can be achieved within one week with a 4–6 fold increase in clonogenic cells. Additionally, methylcellulose assays were used to determine if conditioned medium from HS-5, HS-21, HS-23, and HS-27 could support colony formation. Consistent with the shorter assay only conditioned medium from HS-5 supported the growth of colonies from $38^+$ population and the $38^{lo}$ population. FIG. 3 is a comparative analysis of the activity of HS-5 conditioned medium, HS-21 conditioned medium (with and without serum), and growth factor mix (GF mix). HS-5 conditioned media, independent of serum content, generated an equivalent number of G/GM colonies from $38^{lo}$ cells as the GF mix, however HS-5 conditioned medium generated significantly more colonies from $38^+$ cells (FIG. 3A). In contrast, conditioned medium from HS-21 supported significantly fewer G/GM from both CD34$^+$ subpopulations compared to HS-5 or GF mix. The relative numbers of BFU-E generated by these conditioned media from $38^{lo}$ cells were also significantly different and paralleled the observations with the G/GM colonies (FIG. 3B). However, the GF mix generated significantly more BFU-E from $38^+$ cells than any conditioned medium.

These results indicate that HS-5 and HS-21 secrete significant levels of numerous cytokines. However, only HS-5 can support CFU growth, whereas HS-21 conditioned medium did not support CFU even when concentrated 8-fold. The possibility that HS-21 may contain an inhibitor was ruled out by mixing experiments.

Figure 4A:
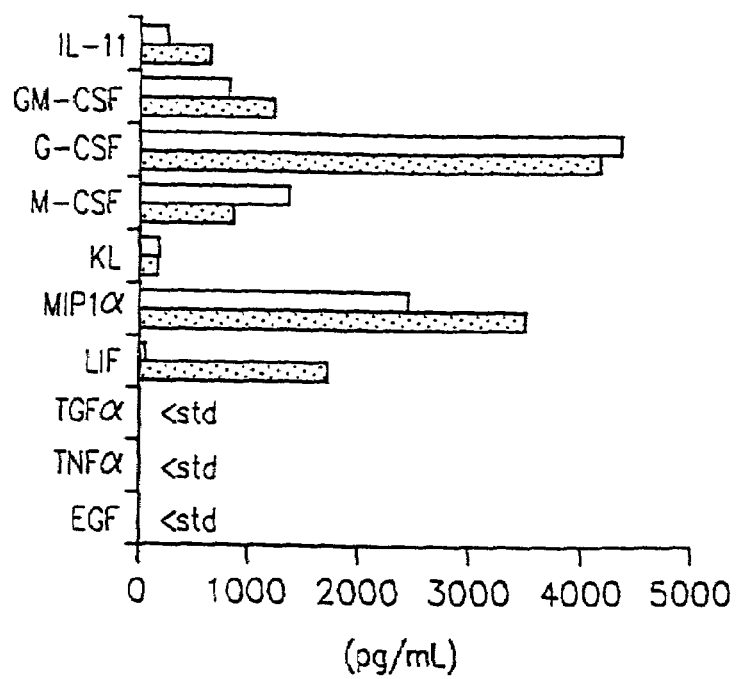
FIGS. 4A and B collectively depict the ELISA results demonstrating the similarity in cytokines secreted by HS-5 (solid bars) and HS-21 (open bars). "<std." indicates that the cytokine level was below the detectable limits of the ELISA, and ">std." indicates that the level was greater than the standard curve. The supernatants were analyzed neat, at 1:2 and 1:5 dilutions. Data represents the concentration from one or more dilutions that were within the standard curve.
Figure 4B:
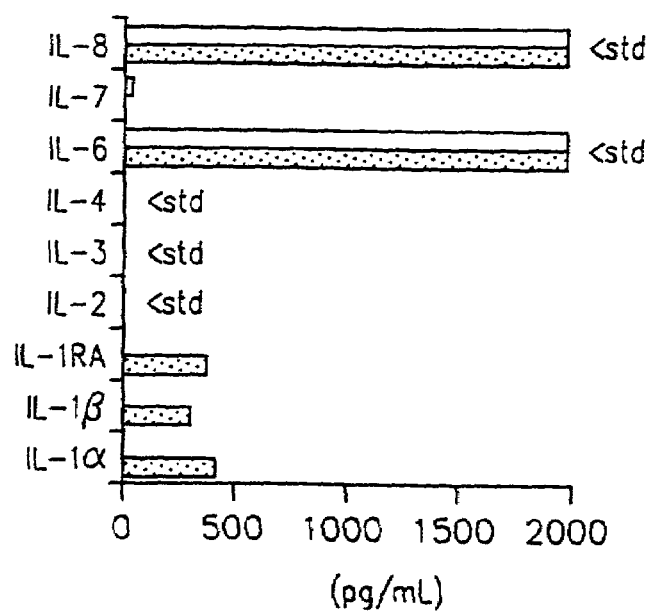

The conditioned media from four cell lines were assayed for the cytokines G-CSF, GM-CSF, KL, LIF, IL-6, IL-1α, IL-3 and IL-11. The results indicated that only HS-5 and HS-21 conditioned medium contained significant amounts of these cytokines, and thus conditioned media from these lines were additionally tested for the presence of IL-1β, IL-IRA, IL-2, IL-7, IL-8, EGF, TNFα, TGFα and MIP-Iα. FIG. 4 demonstrates that the majority of these cytokines were present in HS-5 and HS-21 supernatants at similar levels. HS-5 however, additionally secretes IL-1α, IL-1β, IL-1RA and LIF (at 0.4 to 1.8 ng/ml). Addition of these cytokines to HS-21 supernatants did not support colony formation and neutralizing antibodies did not inhibit HS-5 supernatants. Thus, HS-5 was secreting a cytokine that could support colony formation by itself or in combination with other factors. To identify genes expressed in HS-5 and not in HS-21, a differential display technique was used, identifying two isolated bands which were uniquely expressed by HS-5. IL-3 was not found in any supernatant and was not detectable using rtPCR for IL-3 message in mRNA from the HS-5 or HS-21 cell lines.

Together, these observations suggest that the factors responsible for differentiation and proliferation of committed progenitors are distinct from those required for maintenance of the immature pre-CFC pool. Moreover, it suggests that these maintenance factors are extracellular matrix or membrane associated.

A deposit of the human stromal cell line HS-5 was made on May 5, 1995, on behalf of Fred Hutchinson Cancer Research Center with the American Type Culture Collection, 10801 University Blvd., Manassas, Va., 20110-2209, under the terms of the Budapest Treaty and designated accession number ATCC CRL 11882.

All publications, patents and foreign patent publications are herein incorporated by reference to the same extent as if each individual publication, patent or patent publication was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. An immortalized human stromal cell line which secretes IL-1α and, when cocultured with human hematopoietic precursor cells, expands the number of precursor cells in the coculture from the number initially present.

2. The immortalized human stromal cell line of claim 1, which secretes LIF, KL, MIPI α, and IL-6.

3. The immortalized human stromal cell line of claim 1, which expands the number of human hematopoietic pluripotent precursor cells in the absence of serum.

4. The immortalized human stromal cell line of claim 1, wherein the human hematopoietic pluripotent precursor cells have been separated from a blood product sample isolated from a patient prior to co-culture.

5. The immortalized human stromal cell line of claim 4, wherein the blood product sample is bone marrow, peripheral blood, umbilical cord blood, fetal liver, or spleen.

* * * * *